(12) United States Patent
Kagami et al.

(10) Patent No.: US 11,583,037 B2
(45) Date of Patent: Feb. 21, 2023

(54) MEASURING BOARD AND FOOT SHAPE DATA CREATING SYSTEM

(71) Applicant: ASICS Corporation, Hyogo (JP)

(72) Inventors: Kana Kagami, Hyogo (JP); Norihiko Taniguchi, Hyogo (JP); Kazunari Takeichi, Hyogo (JP)

(73) Assignee: ASICS CORPORATION, Hyogo (JP)

( * ) Notice: Subject to any disclaimer, the term of this patent is extended or adjusted under 35 U.S.C. 154(b) by 198 days.

(21) Appl. No.: 16/904,680

(22) Filed: Jun. 18, 2020

(65) Prior Publication Data

US 2021/0015212 A1 Jan. 21, 2021

Related U.S. Application Data

(63) Continuation of application No. PCT/JP2019/028147, filed on Jul. 17, 2019.

(51) Int. Cl.
| | |
|---|---|
| A43D 1/02 | (2006.01) |
| G01B 3/06 | (2006.01) |
| A43D 1/06 | (2006.01) |
| G01B 11/24 | (2006.01) |
| G01B 3/00 | (2006.01) |
| A61B 5/107 | (2006.01) |

(52) U.S. Cl.
CPC .............. A43D 1/025 (2013.01); A43D 1/06 (2013.01); A61B 5/1074 (2013.01); G01B 3/004 (2013.01); G01B 3/06 (2013.01); G01B 11/24 (2013.01)

(58) Field of Classification Search
USPC ..................... 33/515, 3 R, 3 A, 3 B
See application file for complete search history.

(56) References Cited

U.S. PATENT DOCUMENTS

| | | | | | |
|---|---|---|---|---|---|
| 1,221,557 | A | * | 4/1917 | Madden | A43D 1/02 |
| | | | | | D10/70 |
| 1,430,794 | A | * | 10/1922 | Canfield | A43D 1/02 |
| | | | | | 297/423.14 |
| 2,163,661 | A | * | 6/1939 | Brown | A43D 1/02 |
| | | | | | 33/3 R |

(Continued)

FOREIGN PATENT DOCUMENTS

| | | |
|---|---|---|
| CN | 204908199 U | 12/2015 |
| CN | 108805138 A | 11/2018 |

(Continued)

OTHER PUBLICATIONS

Extended European Search Report issued in corresponding European Patent Application No. 19894394.6, dated Jun. 28, 2021.

(Continued)

*Primary Examiner* — Christopher W Fulton
(74) *Attorney, Agent, or Firm* — McDermott Will & Emery LLP

(57) ABSTRACT

A measuring board having a simple structure is to be provided. A measuring board includes a main body having a foldable structure, and the main body includes a placement part on which a foot is placed and that includes a measurement marker, a wall part provided adjacent to the placement part and configured to position a heel during measurement, and supporting structures and that support the wall part. With such a configuration, a measuring board having a simple structure can be provided.

18 Claims, 13 Drawing Sheets

(56) References Cited

U.S. PATENT DOCUMENTS

| | | | | |
|---|---|---|---|---|
| 5,164,793 | A * | 11/1992 | Wolfersberger | G01B 11/25 33/3 R |
| 6,549,639 | B1 * | 4/2003 | Genest | A61B 5/1074 382/285 |
| 6,834,437 | B1 * | 12/2004 | Kilgore | A61B 5/1074 33/515 |
| 6,983,548 | B1 * | 1/2006 | Cook | A43D 1/02 33/515 |
| 7,051,452 | B2 * | 5/2006 | Brooks | A43D 1/025 33/227 |
| 9,778,027 | B1 | 10/2017 | Smith | |
| 9,955,900 | B2 * | 5/2018 | O'Connor | A61B 5/1032 |
| 10,420,397 | B2 * | 9/2019 | Hei | G06T 7/62 |
| 10,492,569 | B2 * | 12/2019 | Liu | G01B 11/24 |
| 2013/0114869 | A1 | 5/2013 | Hernandez Stark et al. | |
| 2016/0073931 | A1 * | 3/2016 | Ferber | A61B 5/1072 600/592 |
| 2016/0286906 | A1 * | 10/2016 | Malal | G01B 11/2513 |
| 2017/0169571 | A1 | 6/2017 | Hung et al. | |
| 2018/0033202 | A1 | 2/2018 | Lam et al. | |

FOREIGN PATENT DOCUMENTS

| | | | | |
|---|---|---|---|---|
| DE | 102011007678 A1 * | 10/2012 | | A43D 1/025 |
| DE | 102011121086 A1 * | 6/2013 | | A43D 1/025 |
| EP | 1844709 A1 * | 10/2007 | | A43D 1/02 |
| EP | 2586323 A1 | 5/2013 | | |
| FR | 2886108 A1 | 12/2006 | | |
| FR | 3001886 A1 | 8/2014 | | |
| FR | 3060735 A1 | 6/2018 | | |
| JP | S60-154007 U | 10/1985 | | |
| JP | 2001-327304 A | 11/2001 | | |
| JP | 2007-267996 A | 10/2007 | | |
| JP | 2018-164727 A | 10/2018 | | |
| KR | 2020031797 A * | 3/2020 | | A61B 5/1074 |
| WO | 01/77910 A1 | 10/2001 | | |
| WO | 2013/026798 A1 | 2/2013 | | |
| WO | 2015/123518 A1 | 8/2015 | | |
| WO | WO-2017009756 A1 * | 1/2017 | | A43D 1/02 |
| WO | 2017/022045 A1 | 2/2017 | | |
| WO | 2018/007384 A1 | 1/2018 | | |
| WO | WO-2018109421 A1 * | 6/2018 | | A43D 1/025 |
| WO | 2018/109421 A1 | 8/2018 | | |
| WO | WO-2020208298 A1 * | 10/2020 | | A43D 1/025 |

OTHER PUBLICATIONS

International Search Report issued in the corresponding International Patent Application No. PCT/JP2019/028147, dated Oct. 8, 2019, with English translation.

European Office Action issued in corresponding European Patent Application No. 19894394.6, dated Dec. 8, 2022.

* cited by examiner

MEASURING BOARD AND FOOT SHAPE DATA CREATING SYSTEM

CROSS REFERENCE TO RELATED APPLICATIONS

This application is a continuation of International Application No. PCT/JP2019/028147, filed on Jul. 17, 2019, which is incorporated by reference in its entirety.

BACKGROUND OF INVENTION

1. Field of the Invention

The present invention relates to a measuring board and a foot shape data creating system.

2. Description of the Related Art

Measuring boards for measuring foot shapes have been conventionally known and are used when customers purchase shoes in stores, for example. A measuring board is used to measure a longitudinal length of a foot, a foot width, an instep size, or the like (Patent Literature 1, for example).
[Patent Literature 1] Japanese Unexamined Patent Application Publication No. 2001-327304

SUMMARY OF THE INVENTION

With widespread use of the Internet in recent years, when people purchase shoes, the chances to purchase shoes on the Internet, without actually visiting stores, are increasing. Since shoe sizes vary depending on each shoe type or each shoe manufacturer, when shoes are purchased on the Internet, the sizes may sometimes not fit. Therefore, there is a need for enabling purchasers to measure their foot sizes by themselves at home, for example.

The present invention has been made to solve the problem above, and a purpose thereof is to provide a measuring board having a simple structure.

The present invention includes a main body having a foldable structure, and the main body includes a placement part on which a person to be measured places one's foot and that includes a measurement marker, a wall part provided adjacent to the placement part and configured to position a heel of the foot during measurement, and a supporting structure that supports the wall part.

The present invention provides a measuring board having a simple structure.

BRIEF DESCRIPTION OF DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

In the following, an embodiment of the present invention will be described. In the embodiment below, the terms "width direction", "height direction", and "longitudinal direction" may be used to describe directions. A width direction means a width direction of a foot placed on a measuring board. A longitudinal direction means a longitudinal direction of a foot placed on a measuring board. A height direction means a height direction viewed from a person being measured placing a foot on a measuring board. Also, using a three-dimensional Cartesian coordinate system, a width direction of a measuring board may be referred to as an X-axis direction, a longitudinal direction thereof may be referred to as a Y-axis direction, and a height direction thereof may be referred to as a Z-axis direction, for the sake of convenience.

Figure 1:
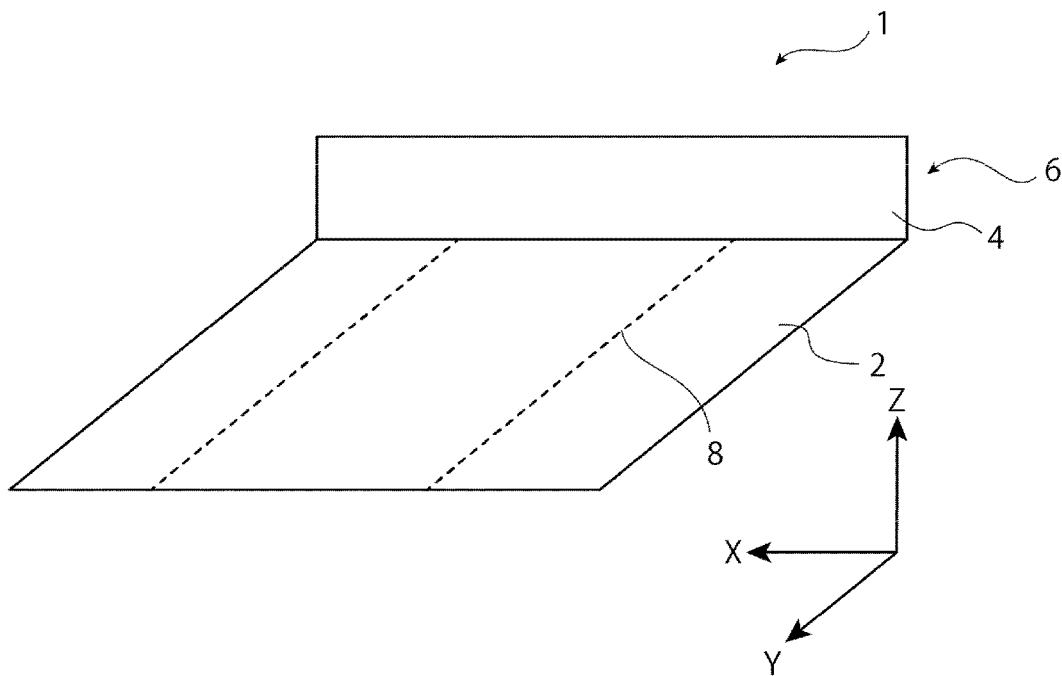
FIG. 1 is a perspective view of a measuring board.

FIG. 1 is a perspective view of a measuring board. In the illustrated example, a measuring board 1 includes a main body 6, which includes a placement part 2 on which a foot is placed, and a wall part 4 used to position a heel. The main body 6 may be suitably formed by folding a sheet of board into a predetermined shape.

The main body 6 may be suitably made of paper that is sufficiently thick and foldable, such as corrugated cardboard. Parts of the main body 6, including the placement part 2 and the wall part 4, are formed by assembling a sheet of paper cut out into a predetermined shape.

The placement part 2 is an area on which a foot is placed during measurement. The placement part 2 includes a plane along an X-Y plane. More specifically, the placement part 2 has a rectangular shape of which a shorter side is longer than a longitudinal length of a foot (40 centimeters, for example) and of which a longer side is equal to or longer than a person's shoulder width (100 centimeters, for example). On the upper surface (the surface on the positive Z direction side) of the placement part 2, measurement markers 8 are provided.

In the illustrated example, the measurement markers 8 are reference lines that each extend parallel with the Y-axis and indicate a reference position for positioning of a foot during measurement. A person to be measured stands such that a line connecting the center of a heel and the tip of the second toe overlaps a reference line (measurement marker 8). As a measurement marker 8, a scale for measurement or a foot shape may also be used, or both such a scale or foot shape and a reference line may be provided. The measurement markers 8 may be suitably printed on the main body 6. Alternatively, sticker-type markers may be stuck as the measurement markers.

The wall part 4 extends almost upright in the height direction (positive Z direction) from one longer side of the placement part 2. The height of the wall part 4 may be 2 centimeters or greater for adults and 1.5 centimeters or greater for children, and may suitably be a height such that the upper end of the wall part 4 is not in contact with a calf. The wall part 4 is a positioning structure with which a heel is brought into contact during measurement. Accordingly, the heel part of a foot shape as a measurement marker 8 is positioned at the wall part 4, and the foot shape is drawn such as to extend in the positive Y direction from the wall part 4. When a scale is used as a measurement marker 8, the position of the wall part 4 is set to zero, and the scale marks are provided at equal intervals, in millimeters for example, from the wall part 4 in the positive Y direction.

Figure 2:
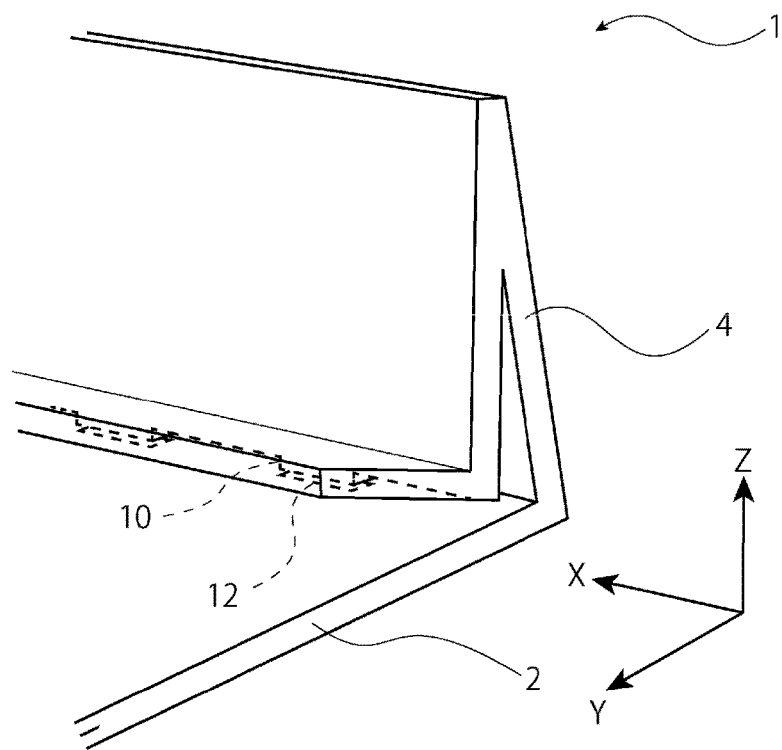
FIG. 2 is a magnified perspective view of the measuring board.

FIG. 2 is a magnified perspective view of the measuring board. As shown in FIG. 2, the measuring board 1 includes a supporting structure for supporting the wall part 4. The supporting structure includes tongues 10 that each are provided at an end of paper constituting the wall part 4, and slits 12 that each are formed nearly at a base position of the wall part 4. When the wall part 4 is formed, the paper is folded twice around the X-axis such that the tongues 10 are fitted into the slits 12, so that the wall part 4 can be vertically supported. The supporting structure also makes the wall to be a double-layered structure of paper. Accordingly, the measuring board 1 made of thin paper may also appropriately support the wall part.

When a person to be measured uses the measuring board, the person to be measured stands on the placement part 2 such that the heels come into contact with the surface of the wall part 4, while referring to the measurement markers 8. By referring to a scale, the person to be measured can measure the length of a foot.

With the measuring board 1 described above, a foot shape can be measured by means of a simple structure. The measuring board 1 of this kind may be prepared by printing the measurement markers 8 on a surface of corrugated cardboard or thin paper. The measuring board 1 is not limited to paper, and may be a thin resin sheet or the like as long as it is foldable. The measuring board 1 made of such a thin material can be distributed as a supplement to a magazine or the like, or can be distributed by postal mail or through the Internet, for example. When the measuring board 1 is distributed as a supplement, a geometric net of the measuring board 1 may be prepared by printing, on a sheet of paper, the placement part 2, the wall part 4, and cutting lines indicating the contour of the measuring board 1. A person to be measured will cut out the measuring board 1 along the cutting lines to assemble the measuring board 1. When print data of the measuring board 1 is distributed through the Internet, image data including the outer form of the main body 6, the position of each tongue 10, the position of each slit 12, and the measurement markers 8 may be prepared to be printed out by a user. The user will process the printed material to assemble the measuring board 1. The printed material may also be pasted over cardboard, such as corrugated cardboard. Since the measuring board 1 is foldable, the storage space therefor can be reduced by folding the measuring board 1 when it is not in use.

Figure 3:
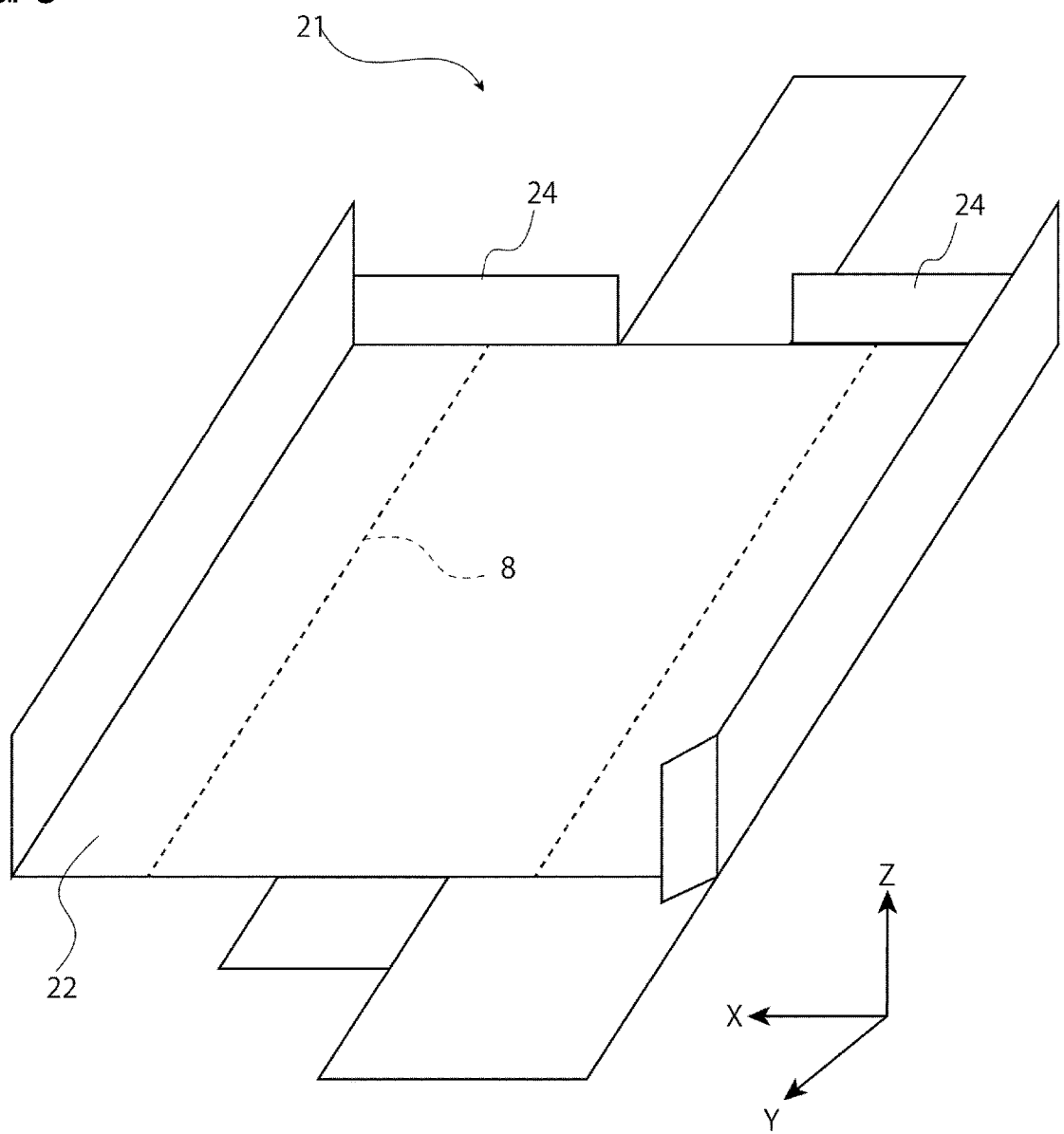
FIG. 3 is a perspective view of a measuring board according to a modification.

FIG. 3 is a perspective view of a measuring board according to a modification. The measuring board shown in FIG. 3 serves dually as a shoebox. More specifically, a measuring board 21 is formed with a shoebox on the inner surface of which a placement part 22, the measurement markers 8, and the like are printed. The measuring board 21 includes the placement part 22 and wall parts 24. The measuring board 21 is formed by opening and flattening the shoebox and then deforming and assembling it. Also in this case, the shoebox may suitably be made by assembling a sheet of corrugated cardboard so that the measuring board 21 can be made by assembling the sheet of corrugated cardboard.

Figure 4:
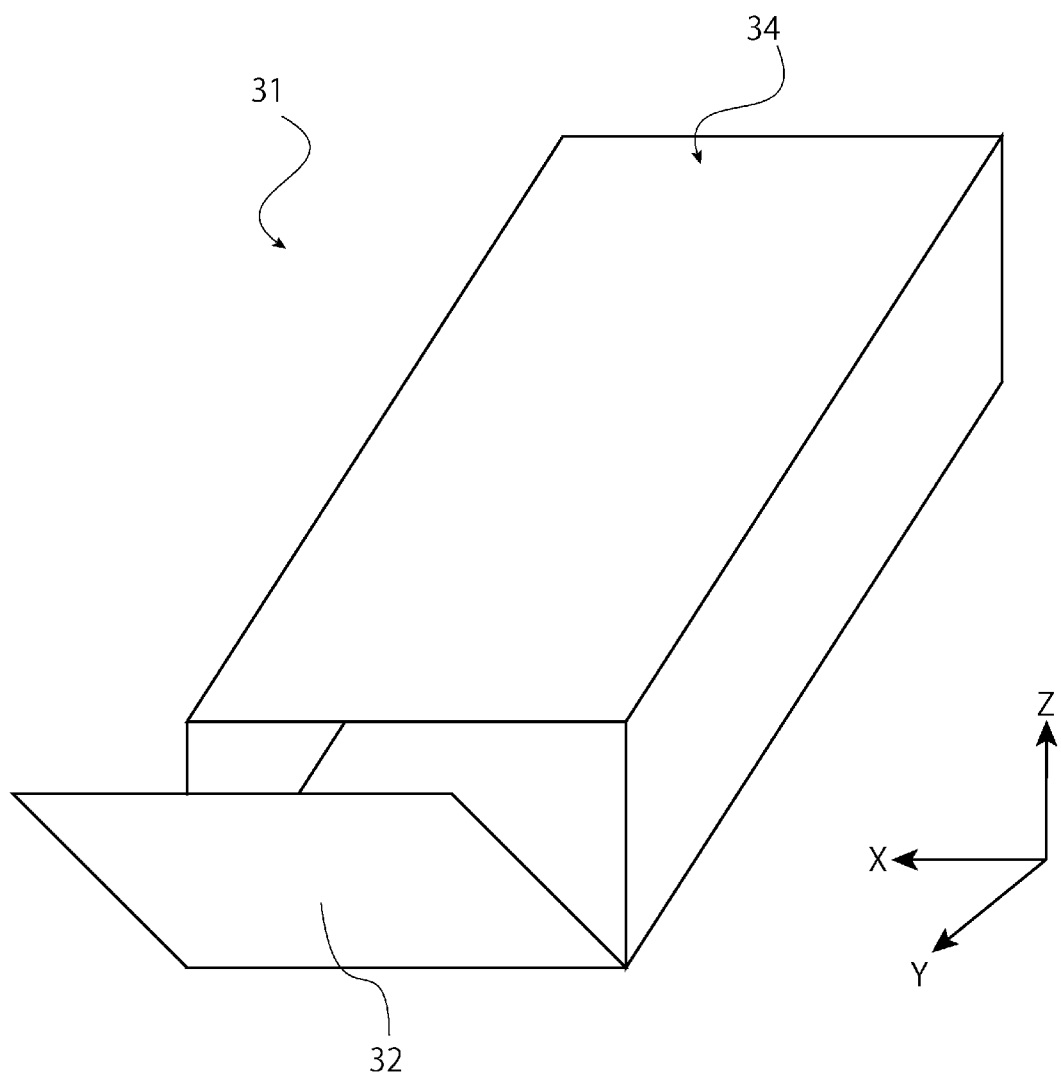
FIG. 4 is a perspective view of a shoebox.

FIG. 4 is a perspective view of a shoebox. A shoebox 31 has a rectangular parallelepiped shape including a lid 32 and a box main body 34 that are integrally formed. The box main body 34 is a box of which an end surface can be opened and closed. The end surface can be opened and closed around the X-axis, and the portion to be opened and closed is the lid 32.

Figure 5:
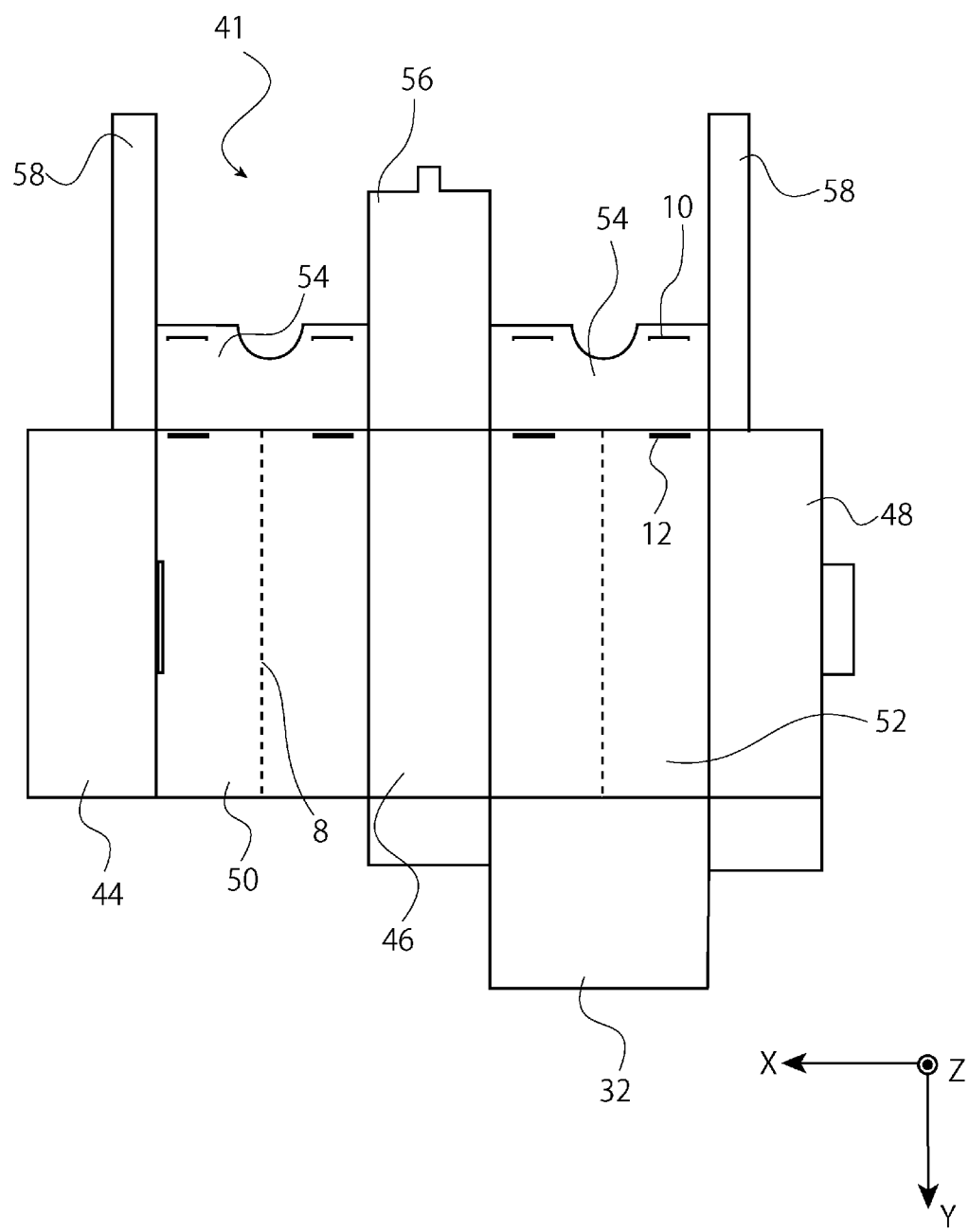
FIG. 5 is an exploded plan view of a measuring board.
Figure 6:
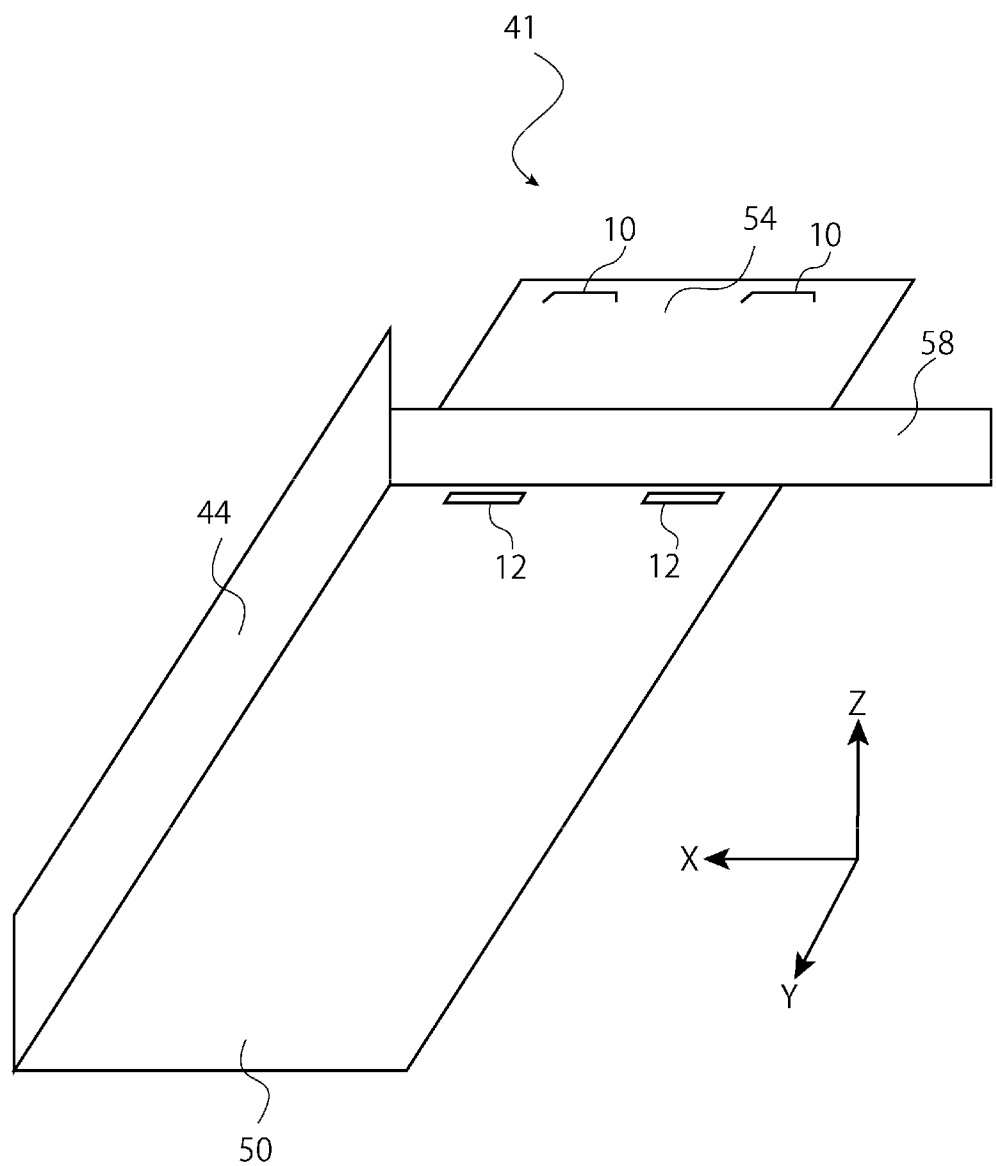
FIG. 6 is a diagram that shows a process step for assembling the measuring board.
Figure 7:
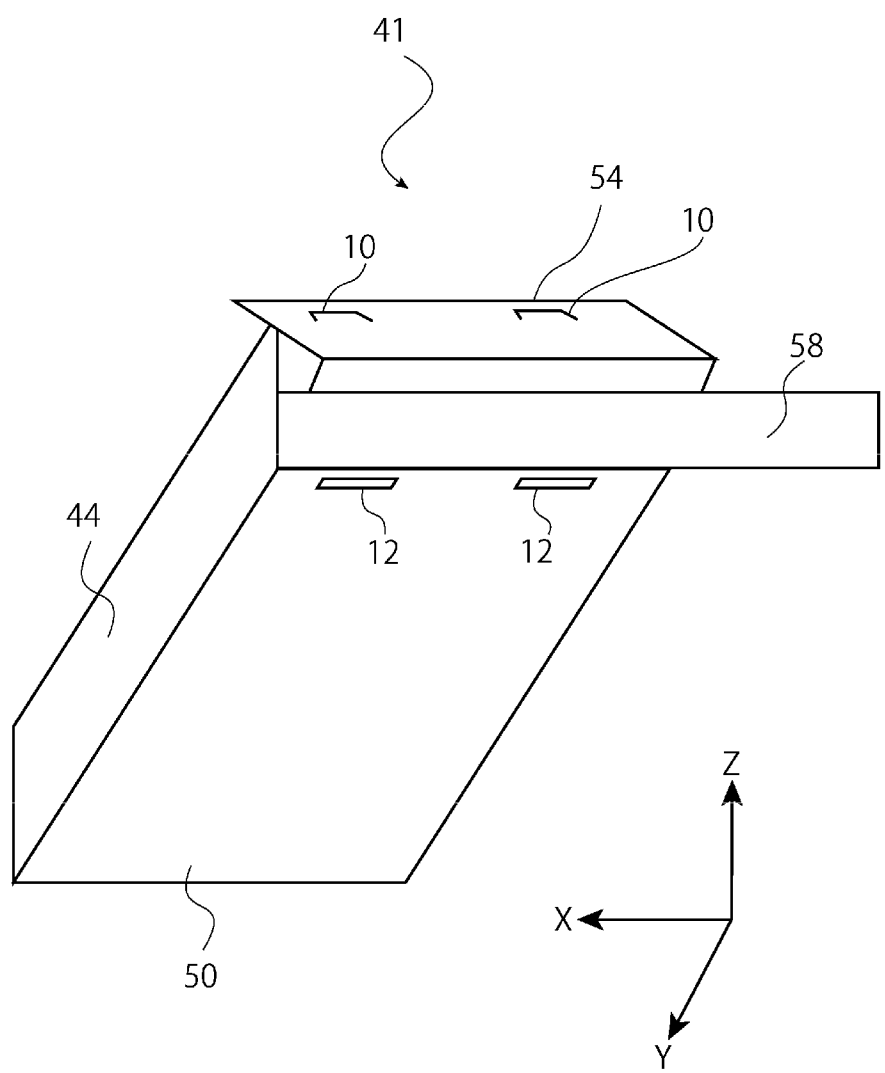
FIG. 7 is a diagram that shows another process step for assembling the measuring board.
Figure 8:
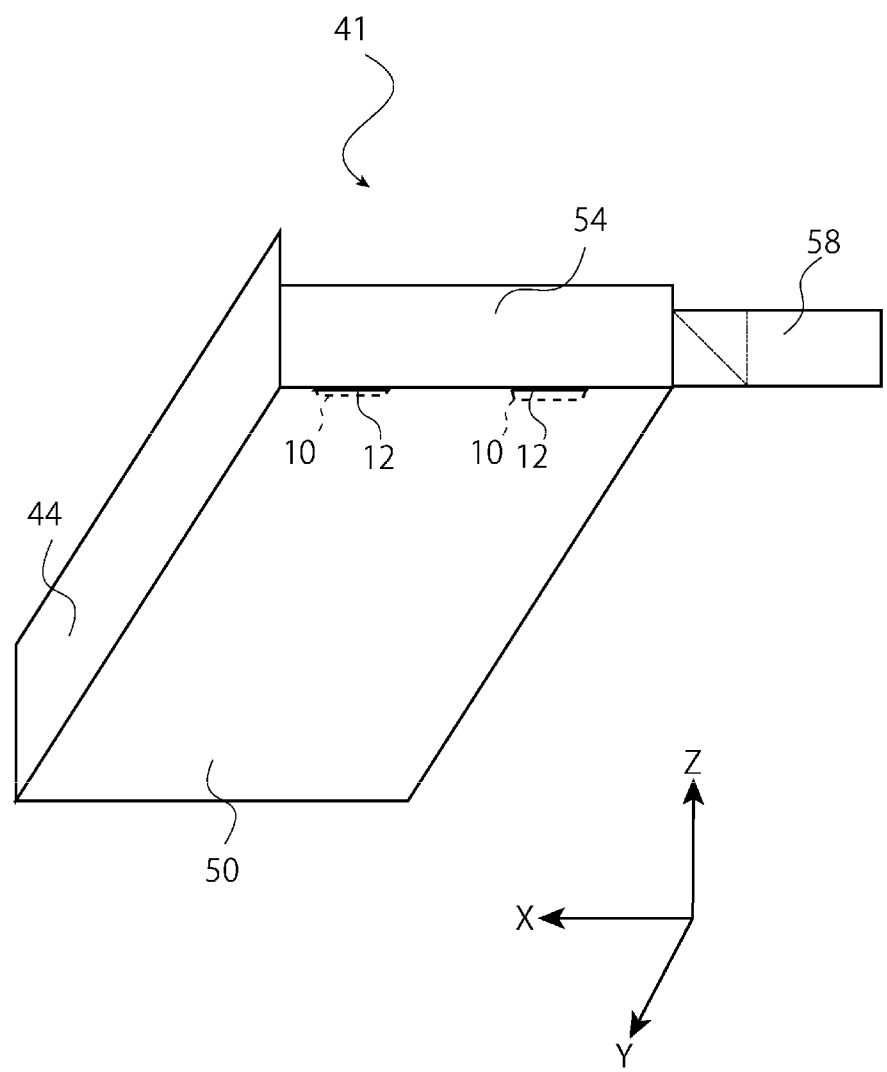
FIG. 8 is a diagram that shows yet another process step for assembling the measuring board.

FIG. 5 is an exploded plan view of a measuring board. In the illustrated example, a measuring board 41 is a sheet of corrugated cardboard including the lid 32, three side surface portions 44, 46, and 48 that form side surfaces of a rectangular parallelepiped, an upper surface portion 50 and a lower surface portion 52 disposed respectively between the three side surface portions 44, 46, and 48, and end surface portions 54 that form an end part on which the lid 32 is not formed. The three side surface portions 44, 46, and 48 are arranged to be spaced away from each other, with the upper surface portion 50 and the lower surface portion 52 provided therebetween, and each of the three side surface portions 44, 46, and 48 has a rectangular shape. Along the X-axis, the side surface portion 44, the upper surface portion 50, the side surface portion 46, the lower surface portion 52, and the side surface portion 48 are arranged in this order, with the longer sides thereof are in contact with each other, such as to form a large rectangular shape. Along the shorter side of each of the upper surface portion 50 and the lower surface portion 52 on the negative Y side, the end surface portion 54 of a substantially rectangular shape is formed. Also, along the shorter side of the lower surface portion 52 on the positive Y side, the lid 32 of a substantially rectangular shape is formed. Further, along the shorter side of the side surface portion 46, located between the upper surface portion 50 and the lower surface portion 52, on the negative Y side, a reinforcement portion 56 is formed to reinforce the end surface portions 54 when the shoebox is formed.

Each end surface portion 54 is also a portion that forms a wall part 4, and has two tongues 10 formed in the end part thereof. Also, two slits 12 are formed near each of the boundary between one end surface portion 54 and the upper surface portion 50 and the boundary between the other end surface portion 54 and the lower surface portion 52. Each tongue 10 has a size such as to be fitted into a slit 12, and, by folding each end surface portion 54 at the center in a Y-axis direction around the X-axis, the tongues 10 can be fitted into the corresponding slits 12. Thus, the wall parts 4 are formed.

The upper surface portion 50, the lower surface portion 52, and the side surface portion 46 located therebetween form the placement part 2. For example, when reference lines are provided as the measurement markers 8, a reference line for one foot may be printed on the upper surface portion 50, and a reference line for the other foot may be printed on the lower surface portion 52. Since the reference lines 8 are formed along a Y direction, which is a long side direction of the upper surface portion 50 and the lower surface portion 52 of the shoebox 31, the left and right feet can be completely placed on the respective surfaces. There is the side surface portion 46 between the upper surface portion 50 and the lower surface portion 52. Since the side surface portion 46 of the shoebox has a width of about 8 to 15 centimeters, a sufficient distance can be ensured between the left and right reference lines. Also, when image capturing of feet is performed using an information processing terminal or the like, as will be described later, image capturing of both the left and right feet can be performed at the same time in one shot, without interference therebetween. Instead of performing image capturing of the left and right feet at the same time, image capturing may be performed multiple times, and image capturing of each foot may be performed separately.

Each of the side surface portions 44 and 48, located at the both ends, is provided with a wall reinforcement portion 58 formed to reinforce a wall part 4. Each wall reinforcement portion 58 has a rectangular shape, of which the longer sides are longer than the shorter sides of the upper surface portion 50 and the lower surface portion 52. When the wall reinforcement portions 58 are assembled, reinforcement structures for reinforcing the wall parts 4 are formed.

Figure 9:
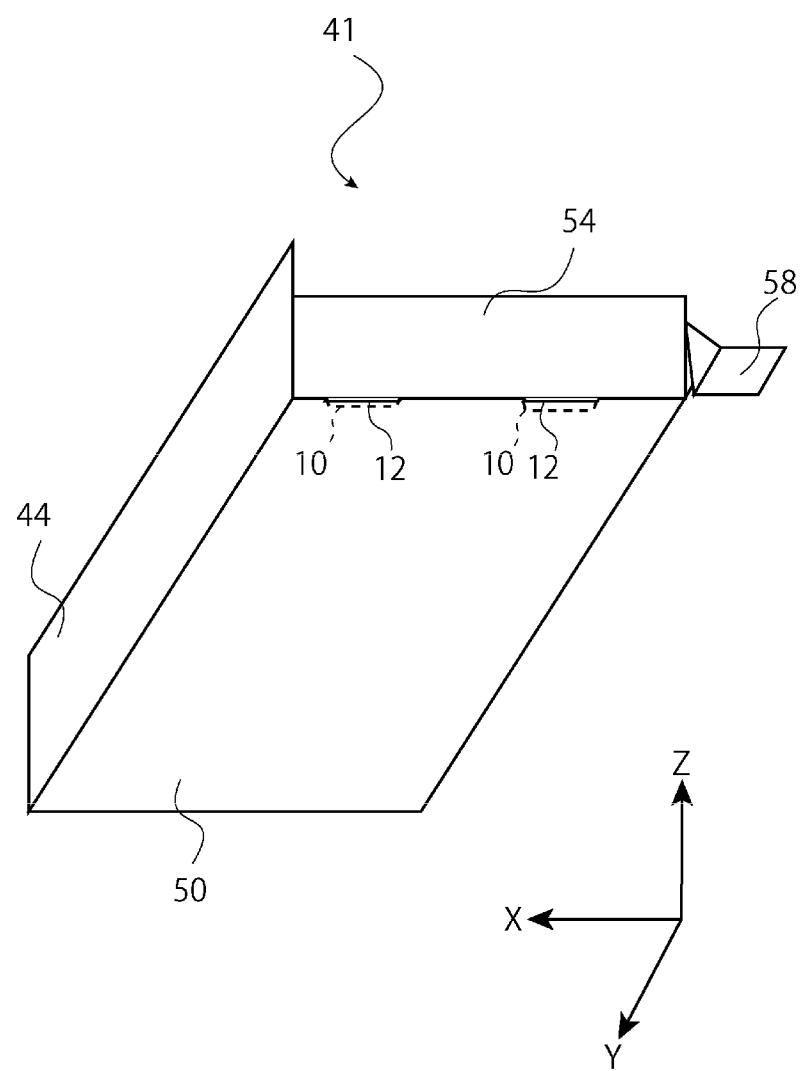
FIG. 9 is a diagram that shows still yet another process step for assembling the measuring board.

FIGS. 6-9 are diagrams that show process steps for assembling the measuring board. FIGS. 6-9 illustrate only part of the measuring board 41 in the interest of clarity. To assemble a wall reinforcement portion 58, before a wall part 4 is formed by an end surface portion 54, the side surface portion 44 located at the both ends is stood up vertically such that the wall reinforcement portion 58 is disposed to extend along the boundary between the end surface portion 54 and the upper surface portion 50 and the boundary between the other end surface portion 54 and the lower surface portion 52 (see FIG. 6). In this state, the end surface portion 54 is folded around the X-axis to form the wall part 4 (see FIG. 7). Subsequently, the tongues 10 in the end surface portion 54 are fitted into the slits 12 (see FIG. 8). In this state, an end of the wall reinforcement portion 58 is protruding from the side surface of the wall part 4. Thereafter, the end of the wall reinforcement portion 58 is folded into a predetermined shape. More specifically, in FIG. 8, the wall reinforcement portion 58 is folded along the dashed dotted line, which is a proportional straight line in an X-Z plane, to form an inverted V shape pointing in the negative Y direction, and then folded along the dashed double-dotted line, which is parallel with the Z-axis, to form a V shape. Accordingly, the end of the wall reinforcement portion 58 is disposed to extend along an X-Y plane, so as to be inserted below the reinforcement portion 56 of the box (see FIG. 9). In FIG. 9, the reinforcement portion 56 of the box is omitted to clarify the illustration.

Since the measuring board 41 can be assembled from the shoebox 31, the shoebox 31 can be reused, and the measuring board 41 can be easily distributed. Also, the wall parts can be reinforced using part of the shoebox 31. By providing perforation or cutting lines along the boundaries between the portions used for the measuring board 21 and the remaining portions, the shoebox 31 can be configured such that the measuring board 21 can be cut out after a purchase of shoes. In this case, the storage space for the measuring board when it is not in use can be further reduced. In consideration of the shape of the measuring board when it is stored, the boundaries may be appropriately determined.

Figure 10:
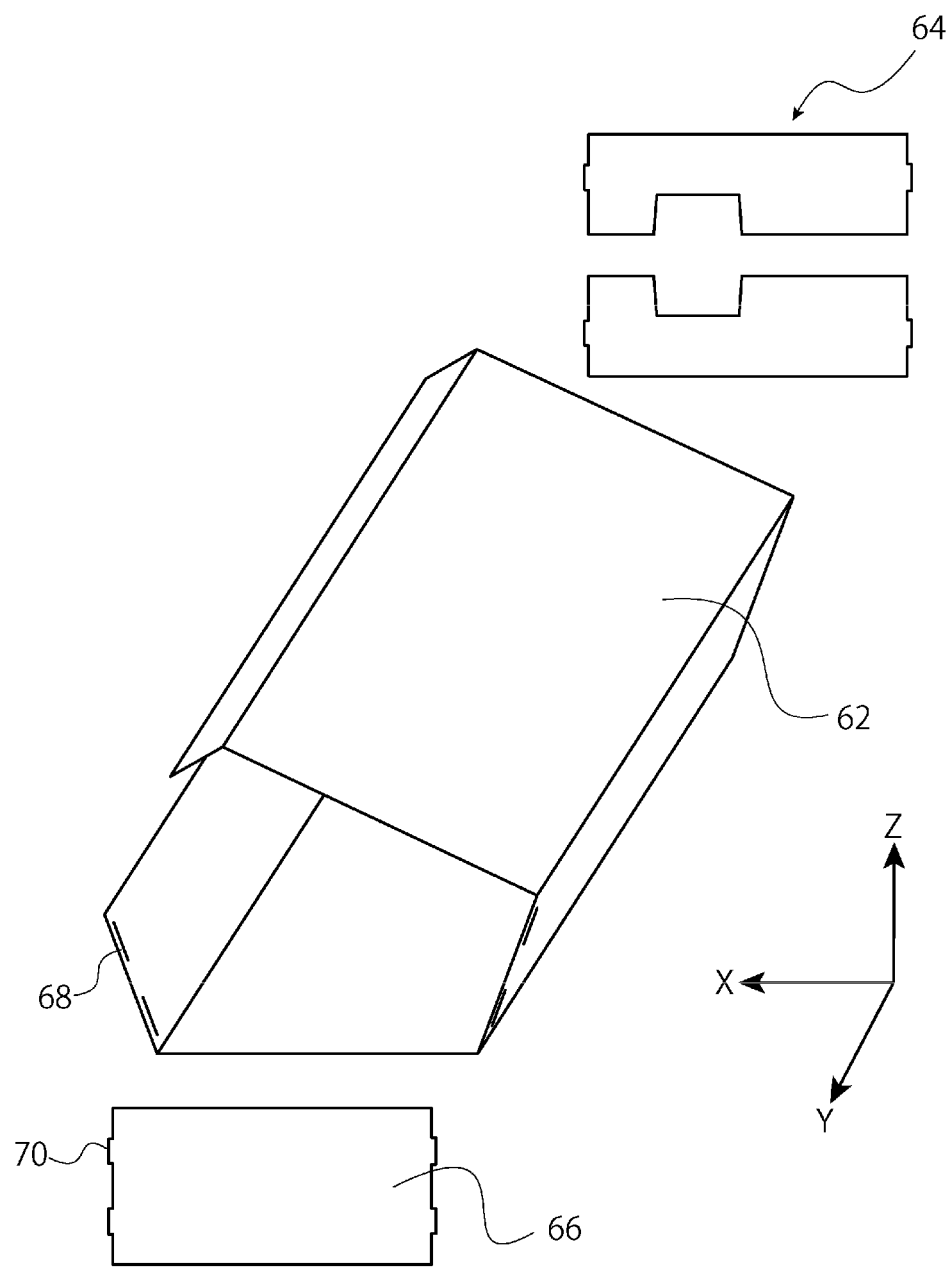
FIG. 10 is an exploded perspective view of a shoebox according to a modification.

FIG. 10 is an exploded perspective view of a shoebox according to a modification. In the example shown in FIG. 10, three side surface portions, an upper surface portion, and a lower surface portion are formed as a single sheet of a box main body 62, and each of first end surface portions 64 and a second end surface portion 66 is formed separately from the box main body 62. The first end surface portions 64 are constituted by an upper portion and a lower portion. The box main body 62 including the three side surface portions, the upper surface portion, and the lower surface portion of the shoebox is folded along the boundaries between the portions around the Y-axis, so as to form a cylindrical shape having a rectangular cross section. The first end surface portions 64 and the second end surface portion 66 are then fitted into the open end surfaces of the cylindrical shape, so that the shoebox is formed. The second end surface portion 66 serves as the lid of the shoebox. In the box main body 62 having the cylindrical shape, multiple slits 68 are formed, whereas tongues 70 to be fitted into the slits 68 are formed in the circumferential parts of the lid portion and the end surface portions. By fitting the tongues 70 into the slits 68, the shoebox is integrated.

Figure 11:
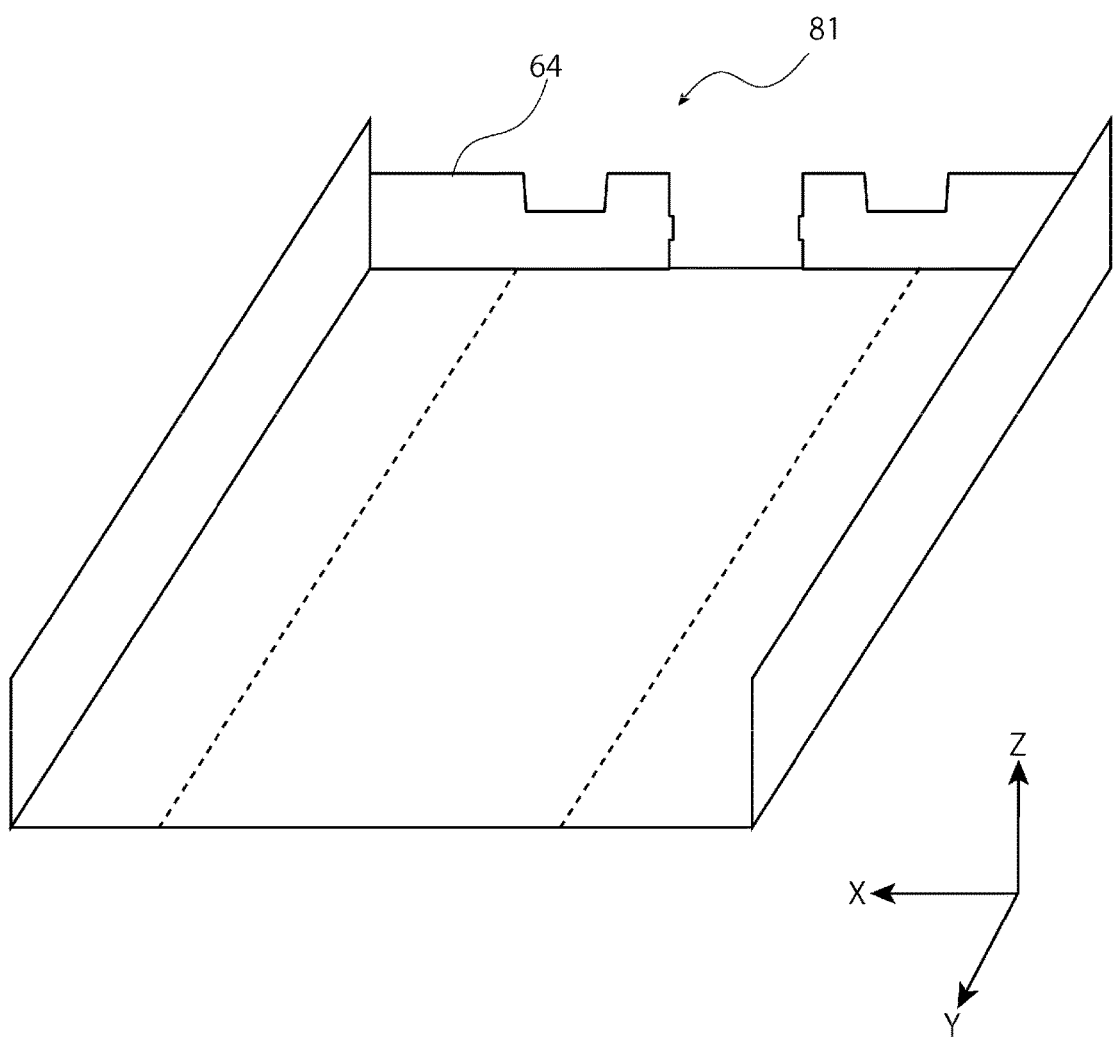
FIG. 11 is a perspective view of a measuring board assembled after the shoebox is opened and flattened.

FIG. 11 is a perspective view of a measuring board assembled after the shoebox is opened and flattened. A measuring board 81 is formed by opening and flattening the box main body 62 including the three side surface portions, the upper surface portion, and the lower surface portion, and by fitting the tongues 70 formed in the upper portion and the lower portion of the end surface portions 64 into the slits 68 formed in the flattened corrugated cardboard. Accordingly, the upper portion and the lower portion form the wall parts 4.

Figure 12:
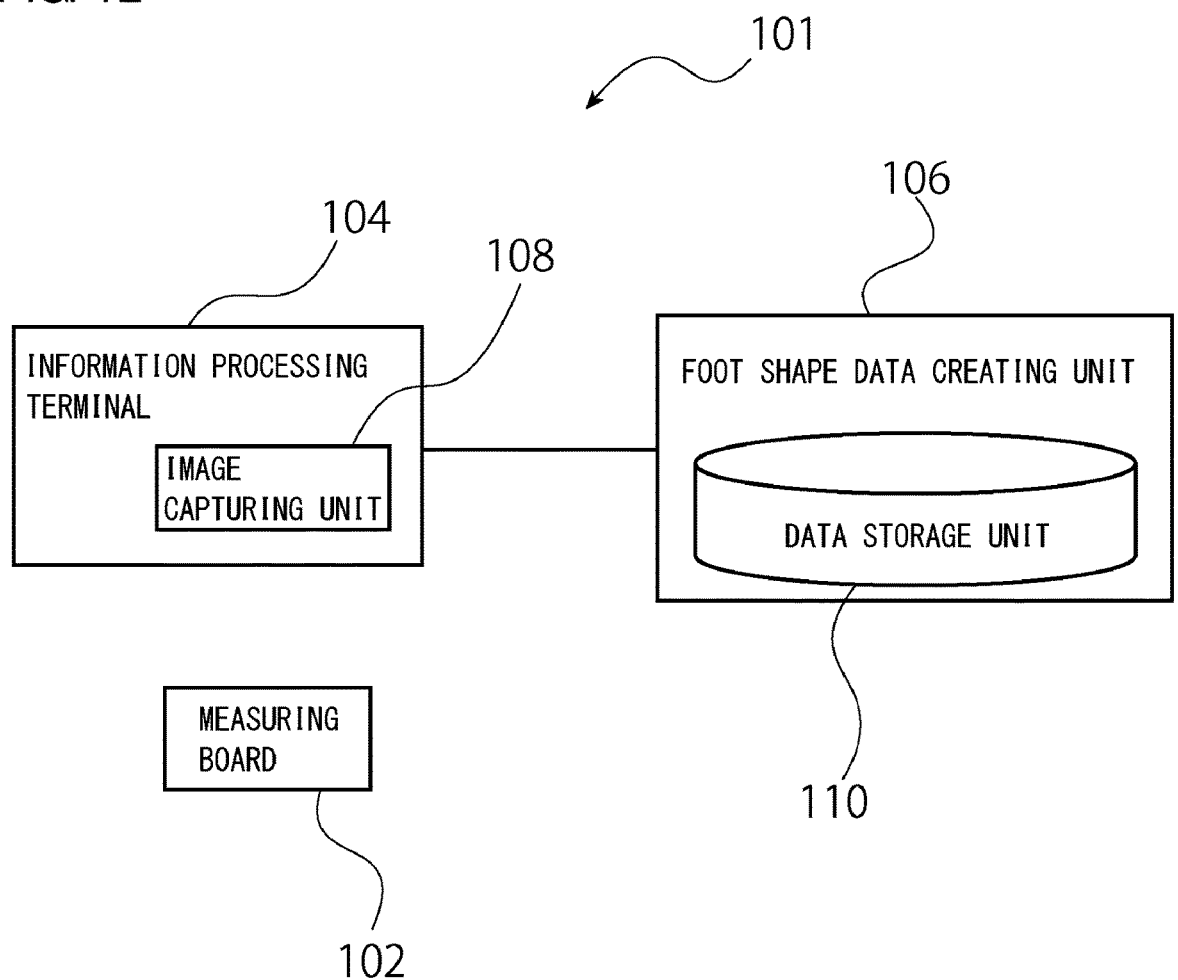
FIG. 12 is a block diagram of a foot shape data creating system.

FIG. 12 is a block diagram of a foot shape data creating system. A foot shape data creating system 101 captures an image of a foot placed on a measuring board 102 and generates foot shape data based on the captured image. As shown in FIG. 12, the foot shape data creating system 101 includes the measuring board 102, an information processing terminal 104 having an image capturing function, and a foot shape data creating unit 106.

For the information processing terminal 104, any terminal provided with a communication function and an image capturing function, such as a camera-equipped cellular phone, may be used. A person to be measured places the feet on the placement part of the measuring board, captures an image of the feet by means of an image capturing unit 108, and transmits the image to the foot shape data creating unit 106.

The foot shape data creating unit 106 is constituted by an external server or the like. The foot shape data creating unit 106 includes a data storage unit 110 that stores image data transmitted from the person to be measured or other users in the past, and foot shape data obtained by analyzing the image data, for example. In addition to such foot shape data, the data storage unit 110 may also store foot shape data held by manufacturers. By referring to a data set stored in the data storage unit 110, the foot shape data creating unit 106 generates foot shape data.

When the foot shape data creating unit 106 is implemented by artificial intelligence, the foot shape data creating unit 106 holds a learned model obtained by performing supervised learning on a data set stored in the data storage unit 110. When image data from a person to be measured is input to the foot shape data creating unit 106, the foot shape data creating unit makes a learned model to work and generates foot shape data for a foot of which an image has been newly captured. The foot shape data creating unit 106 may also perform weighting when generating foot shape data, using information related to foot shapes, such as the gender, age, and nationality of the person to be measured. When the foot shape data creating unit 106 is implemented by artificial intelligence, foot shape data can be transmitted to the person to be measured nearly in real time. Therefore, the person to be measured can obtain accurate foot shape data nearly in real time while staying at home.

The foot shape data includes at least information regarding a foot size (length) and may also include information regarding a foot width and a foot height (three-dimensional data). Generated foot shape data is transmitted to the information processing terminal 104. The data storage unit 110 may also store data other than the foot shape data, such as sales data of shoes held by manufacturers, survey data regarding preference of the person to be measured or other users for shoes, and data regarding characteristics or use environments of shoes, so that shoes can be selected using such various data. Accordingly, information regarding the type and size of shoes recommended based on such data and the foot shape data may be additionally transmitted. The foot shape data creating unit 106 need not necessarily be a server and may be provided in the information processing terminal 104.

Figure 13:
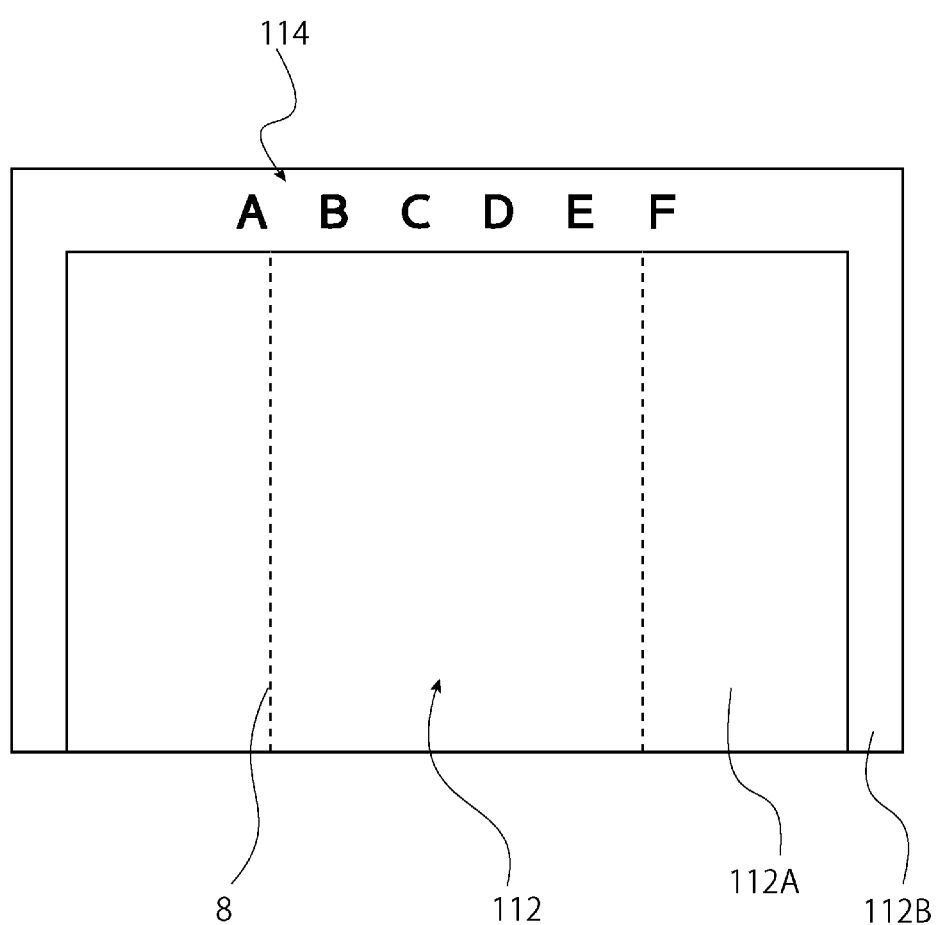
FIG. 13 is a plan view that shows an example of the placement part.

FIG. 13 is a plan view that shows an example of the placement part. When an image of a placement part 112 is captured using an information processing terminal, the distance from the placement part 112 at the time of image capturing and the image capturing angle are different depending on each person. Accordingly, a reference marker 114 is provided as a measurement marker on the placement part 112 to improve the image analysis accuracy. In this case, the placement part 112 includes a placement area 112A on which feet are placed, and a calibration area 112B formed around the placement area 112A. The placement area 112A and the calibration area 112B are colored in single colors different from each other. In order to improve image identification accuracy, the placement area 112A may suitably be colored in a cool color including a neutral color, particularly in a vivid or bright color, and the calibration area 112B may suitably be colored more deeply than the placement area 112A. The reference marker 114 is provided at an arbitrary position in the calibration area 112B and colored in a single color or multiple colors different from the colors of the placement area 112A and the calibration area 112B. In the case of FIG. 13, the calibration area 112B is provided along the three sides of the placement area 112A on the outer peripheral side thereof, along which the wall part 4 is not provided. The calibration area 112B is not limited to the illustrated example, and the contour of the calibration area 112B may be freely set as long as it does not interfere with the range where feet are placed. Similarly, the reference marker 114 may be provided in the placement area 112A if the reference marker 114 is distinguishably colored. The reference marker 114 is a two-dimensional pattern extending over an X-Y plane, and may suitably be a figure, a character, or a combination thereof. The reference marker 114 is used to calculate the image capturing distance when a captured image of the placement part 112 is analyzed. In this case, when image capturing of the placement part 112 is performed, an image of the reference marker 114 is also captured together with the feet as the image capture target, using an information processing terminal, for example. Since the size of the reference marker 114 is determined in advance, the foot shape data creating unit 106 receives an image and calculates the image capturing distance based on the size of the reference marker 114 in the image. Based on the calculation of the image capturing distance, the size of a foot in the image can be measured. Thus, with the reference marker 114, highly-accurate foot shape data can be created by simple measuring operation. Also, the state of recognition of the reference marker 114 may be set as a condition for permitting image capturing.

Figure 14:
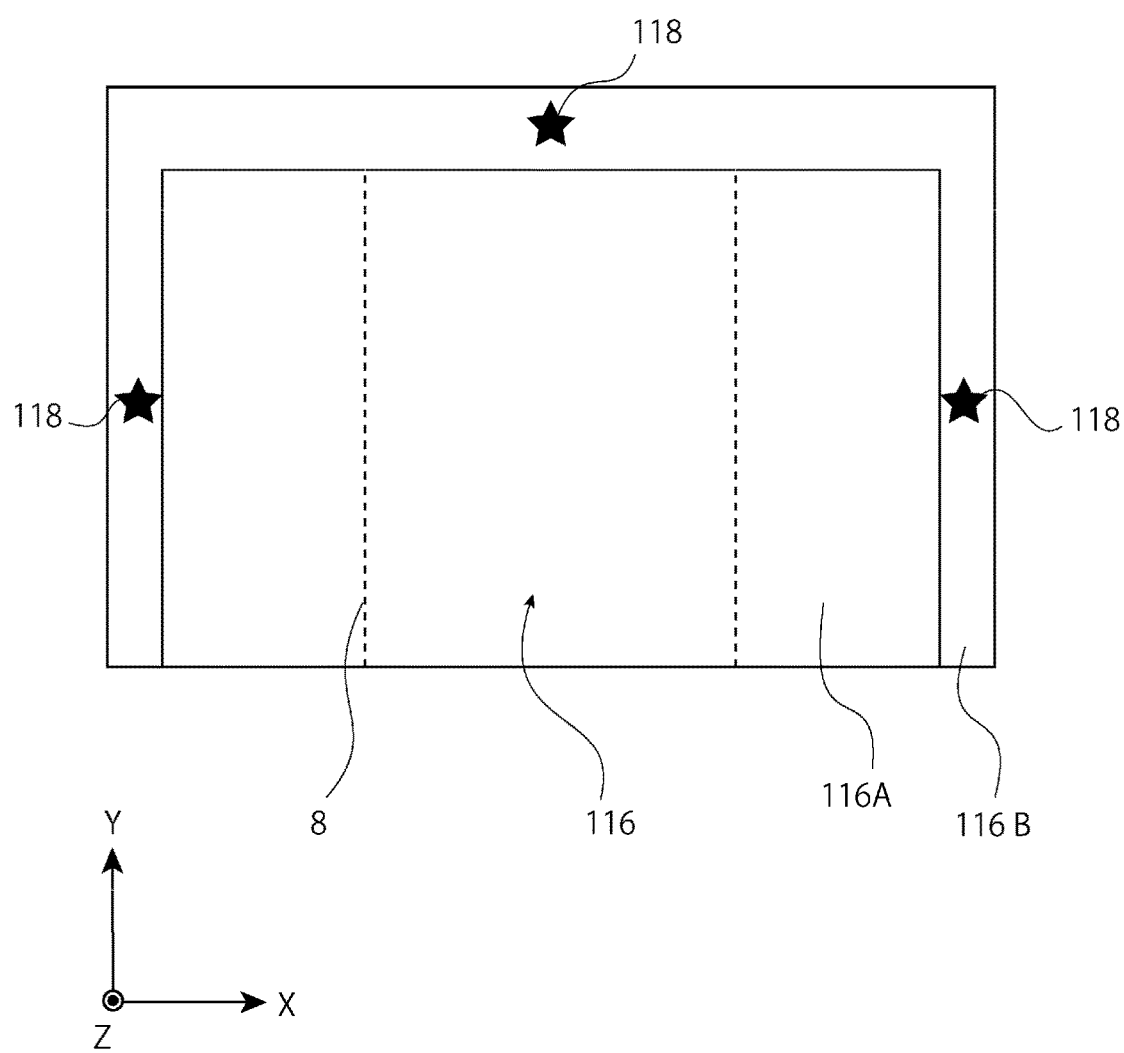
FIG. 14 is a plan view that shows another example of the placement part.

FIG. 14 is a plan view that shows another example of the placement part. On a placement part 116 in the example shown in FIG. 14, distortion correction markers 118 are printed as measurement markers. The placement part 116 includes a placement area 116A on which feet are placed, and a calibration area 116B formed around the placement area 116B. The placement area 116A and the calibration area 116B are colored in single colors different from each other. The distortion correction markers 118 are provided at arbitrary positions in the calibration area 116B and colored in a single color or multiple colors different from the colors of the placement area 116A and the calibration area 116B. In the case of FIG. 14, the calibration area 116B is provided along the three sides of the placement area 116A on the outer peripheral side thereof, along which the wall part 4 is not provided. The calibration area 116B is not limited to the illustrated example, and the contour of the calibration area 116B may be freely set as long as it does not interfere with the range where feet are placed. Similarly, the distortion correction markers 118 may be provided in the placement area 116A if they are distinguishably colored. The distortion correction markers 118 are at least three marks arranged at distant positions on an X-Y plane. The multiple distortion correction markers 118 may have any shapes as long as an image of them can be clearly captured by means of the image capturing function of an information processing terminal. All the distortion correction markers 118 may have the same shape, or may have different shapes. Although the distortion correction markers 118 in the illustrated example are provided at positions corresponding respectively to the three sides of the placement area 116B, the positions of the distortion correction markers 118 are not limited thereto. As illustrated in FIG. 14, the three distortion correction markers 118 are not arranged linearly on an X-Y plane. Image capturing may be performed such that all the distortion correction markers 118 are included in the image.

By analyzing a captured image of the placement part 116 provided with such distortion correction markers 118, the distance between the information processing terminal and the placement part 116 and the angle of the information processing terminal at the time of image capturing can be calculated based on the positions of the distortion correction markers 118. Accordingly, the foot shape data creating unit 106 calculates the distance between the information processing terminal and the placement part 116 and the angle of the information processing terminal at the time of image capturing based on the positions of the distortion correction markers 118, and corrects the size of a foot of which an image has been captured, based on the calculation results. Thereafter, the foot shape data creating unit 106 creates a foot shape data based on the corrected foot size.

The present invention is not limited to the aforementioned embodiment, and modifications may be appropriately made to each configuration in the embodiment without departing from the scope of ideas of the present invention.

When the embodiment set forth above is generalized, the following aspects are derived.

Aspect 1

A measuring board, comprising a main body having a foldable structure, the main body comprising:

a placement part on which a person to be measured places one's foot and that includes a measurement marker;

a wall part provided adjacent to the placement part and configured to position a heel of the foot during measurement; and a supporting structure that supports the wall part.

With this configuration, a measuring board having a simple structure can be provided.

Aspect 2

The measuring board according to Aspect 1, wherein the measurement marker is a scale used to measure a length of the foot.

With this configuration, a foot length can be measured without using any device other than the measuring board.

Aspect 3

The measuring board according to Aspect 1 or 2, wherein the measuring board is used to measure a foot shape by means of an image capturing device, and the measurement marker is a reference line extending in a longitudinal direction of the measuring board and indicating a reference position of the foot during measurement.

With this configuration, when a terminal having an image capturing function is used in addition to the measuring board and when the terminal uses a reference line, a foot size can be accurately calculated.

Aspect 4

The measuring board according to Aspect 3, wherein the placement part includes a placement area on which the person to be measured places one's foot and also includes a calibration area provided on the outer peripheral side of the placement area, the placement area excluding the reference line is single colored, and the color of the calibration area is different from the color of the placement area.

With this configuration, image analysis accuracy can be improved.

Aspect 5

The measuring board according to Aspect 4, wherein the measurement marker includes a reference marker that provides a reference size for foot shape measurement, and the reference marker is provided in the calibration area.[0048] With this configuration, foot shape analysis accuracy can be improved.

Aspect 6

The measuring board according to Aspect 4, wherein the measurement marker includes a distortion correction marker for foot shape measurement, used to correct distortion in an image captured by the image capturing device, and the distortion correction marker is provided in the calibration area.

With this configuration, foot shape analysis accuracy can be improved.

Aspect 7

The measuring board according to any one of Aspects 1 through 6, wherein the main body is made of paper.

With this configuration, the entire measuring board can be made thinner and easily stored. Also, the measuring board can be used as a supplement to a magazine or the like, or can be sent by postal mail. Further, by distributing image data of the measuring board via a network, the measuring board can be easily output using a home printer or the like.

Aspect 8

The measuring board according to any one of Aspects 1 through 7, further comprising a reinforcement structure that reinforces the wall part.

With this configuration, even when the strength of the main body itself is insufficient, the wall part can be reinforced.

Aspect 9

The measuring board according to any one of Aspects 1 through 8, wherein the main body is printed on an inner surface of a shoebox.

With this configuration, the measuring board can be distributed during sale of shoes.

Aspect 10

A foot shape data creating system, comprising:

a measuring board comprising a main body having a foldable structure, the main body comprising a placement part on which a person to be measured places one's foot and that includes a measurement marker, a wall part provided adjacent to the placement part and configured to position a heel of the foot during measurement, and a supporting structure that supports the wall part; and a foot shape data creating unit that generates, based on image data of an image captured by an information processing terminal after the foot is placed on the placement part by means of the wall part and also based on a learned model stored in a data storage unit, foot shape data for the foot of which an image has been captured.

With this configuration, foot shape data can be generated using a measuring board having a simple structure.

Aspect 11

The foot shape data creating system according to aspect 10, wherein the foot shape data creating unit is provided in a server provided separately from the information processing terminal, and the server receives the image data of an image captured by the information processing terminal, generates the foot shape data, and transmits the foot shape data to the information processing terminal.

With this configuration, foot shape data can be transmitted using a measuring board having a simple structure.

What is claimed is:

1. A measuring board for measuring a shape of a foot using an image capturing device, the measuring board comprising a main body having a foldable structure, the main body comprising:

a placement part on which a foot to be measured is placed, the placement part including a measurement marker;

a wall part provided adjacent to the placement part and configured to position a heel of the foot during measurement; and a supporting structure that supports the wall part, and wherein the measurement marker is a reference line for at least connecting the center of a heel and the tip of the second toe and extending in a longitudinal direction of the measuring board.

2. The measuring board according to claim 1, wherein the placement part includes a placement area on which the foot is placed and also includes a calibration area provided on the outer peripheral side of the placement area, the placement area excluding the reference line is single colored, and the color of the calibration area is different from the color of the placement area.

3. The measuring board according to claim 2, wherein the measurement marker includes a reference marker that provides a reference size for foot shape measurement, and the reference marker is provided in the calibration area.

4. The measuring board according to claim 2, wherein the measurement marker includes a distortion correction marker for foot shape measurement, used to correct distortion in an image captured by the image capturing device, and the distortion correction marker is provided in the calibration area.

5. The measuring board according to claim 2, wherein the calibration area is provided along the side of the placement area on the outer peripheral side thereof, along which the wall part is not provided.

6. The measuring board according to claim 1, wherein the main body is made of paper.

7. The measuring board according to claim 1, wherein the main body is foldable and is formed with a portion of a shoebox.

8. A foot shape data creating system, comprising:
a measuring board comprising a main body having a foldable structure, the main body comprising
a placement part on which a foot to be measured is placed, the placement part including a measurement marker, wherein the measurement marker is a reference line for at least connecting the center of a heel and the tip of the second toe and extending in a longitudinal direction of the measuring board,
a wall part provided adjacent to the placement part and configured to position a heel of the foot during measurement, and
a supporting structure that supports the wall part;
data storage storing a learned model built based on training data related to various foot shapes; and
a foot shape data creating unit that (1) receives image data from the image capturing device that captures the image of the foot placed on the placement part, and (2) generates, based on the image data and the learned model, foot shape data for the foot of which an image has been captured.

9. The foot shape data creating system according to claim 8, wherein the foot shape data creating unit is provided in a server provided separately from the image capturing device, and the server receives the image data of an image captured by the image capturing device, generates the foot shape data, and transmits the foot shape data to the image capturing device.

10. The foot shape data creating system according to claim 8,
wherein the measurement marker is a scale used to measure a length of the foot, and
wherein the placement part is printed on an inner surface of a shoebox.

11. The foot shape data creating system according to claim 8,
wherein the measuring board is used to measure a foot shape,
wherein the measurement marker is a reference line extending in a longitudinal direction of the measuring board and indicating a reference position of the foot during measurement, and
wherein the placement part is printed on an inner surface of a shoebox.

12. The foot shape data creating system according to claim 8,
wherein the measuring board is used to measure a foot shape,
wherein the placement part includes (1) a placement area on which the foot is placed and (2) a calibration area provided on the outer peripheral side of the placement area,
wherein the placement area excluding the reference line is single colored,
wherein the color of the calibration area is different from the color of the placement area,
wherein the measuring board further comprises a reinforcement structure that reinforces the wall part, and
wherein the placement part is printed on an inner surface of a shoebox.

13. The foot shape data creating system according to claim 8,
wherein the measuring board is used to measure a foot shape,
wherein the placement part includes (1) a placement area on which the foot is placed and (2) a calibration area provided on the outer peripheral side of the placement area,
wherein the placement area excluding the reference line is single colored,
wherein the color of the calibration area is different from the color of the placement area, and
wherein the placement part is printed on an inner surface of a shoebox.

14. The foot shape data creating system according to claim 8,
wherein the measuring board is used to measure a foot shape,
wherein the placement part includes (1) a placement area on which the foot is placed and (2) a calibration area provided on the outer peripheral side of the placement area,
wherein the placement area excluding the reference line is single colored,
wherein the color of the calibration area is different from the color of the placement area,
wherein the placement part includes a reference marker that provides a reference size for foot shape measurement, and the reference marker is provided in the calibration area, and
wherein the placement part is printed on an inner surface of a shoebox.

15. The foot shape data creating system according to claim 8,
wherein the measuring board is used to measure a foot shape,
wherein the placement part includes (1) a placement area on which the foot is placed and (2) a calibration area provided on the outer peripheral side of the placement area,
wherein the placement area excluding the reference line is single colored,
wherein the color of the calibration area is different from the color of the placement area,
wherein the measurement marker includes a distortion correction marker for foot shape measurement, used to correct distortion in an image captured by the image capturing device, and the distortion correction marker is provided in the calibration area, and
wherein the placement part is printed on an inner surface of a shoebox.

16. The foot shape data creating system according to claim 8,
wherein the main body is made of paper, and
wherein the measuring board further comprises a reinforcement structure that reinforces the wall part.

17. The foot shape data creating system according to claim 8,
wherein the measuring board further comprising a reinforcement structure that reinforces the wall part; and
wherein the placement part is printed on an inner surface of a shoebox.

18. The foot shape data creating system according to claim 8, wherein the placement part is printed on an inner surface of a shoebox.

* * * * *